United States Patent [19]
Ennis et al.

[11] Patent Number: 5,939,254
[45] Date of Patent: Aug. 17, 1999

[54] METHODS AND REAGENTS FOR RAPID DIAGNOSIS OF DENGUE VIRUS INFECTION

[75] Inventors: Francis A. Ennis, Shrewsbury, Mass.; T. Mirawati Sudiro, Jakarta, Indonesia; Hiroaki Ishiko, Fujimi, Japan

[73] Assignee: University of Massachusetts, Worcester, Mass.

[21] Appl. No.: 08/840,344

[22] Filed: Apr. 28, 1997

[51] Int. Cl.$^6$ ............... C12Q 1/68; C12Q 1/70; C07H 21/04
[52] U.S. Cl. ............... 435/5; 435/6; 536/24.33
[58] Field of Search ............... 435/5, 6; 536/24.33

[56] References Cited

PUBLICATIONS

Blok et al., Virology 187, 573–590, 1992.
Brown et al., Transactions of the Royal Society of Tropical Medicine and Hygiene 90, 140–143, 1996.
Fu et al., Virology 188, 953–958, 1992.
Mackow et al., Virology 159, 217–228, 1987.
Osatomi et al., Virology 176, 643–647, 1990.
Chan et al., "The influence of antibody levels in dengue diagnosis by polymerase chain reaction," *J. Virol. Methods*, 49:315–322, 1994.
Chang et al., "An integrated target sequence and signal amplification assay, reverse transcriptase–PCR–enzyme . . . ," *J. Clin. Microbiol.*, 32:477–483, 1994.
Chungue et al., "Ultra–rapid, simple, sensitive, and economical silica for extraction of dengue viral RNA from clinical . . . ," *J. Med. Virol.*, 40:142–145, 1993.
Deubel et al., "Identification of dengue sequences by genomic amplification: rapid diagnosis of dengue virus . . . ," *J. Virol. Methods*, 30:41–54, 1990.
Henchal et al., "Sensitivity of a universal primer set for the rapid diagnosis of dengue virus infections by polymerase chain . . . ," *Am. J. Trop. Med. Hyg.*, 45:418–428, 1991.
Hino et al., "Serial Assay of Hepatitis C Virus RNA in Serum for Predicting Response to Interferon–α Therapy," *Digestive Diseases and Science*, 40(1):14–20, 1995.
Kato et al., "Quantification of Hepatitis C Virus by Competitive Reverse Transcription–Polymerase Chain Reaction: Increase of the Virus in Advanced Liver Disease," *Hepatology*, 18(1):16–20, 1993.
Lanciotti et al., "Rapid detection and typing of dengue viruses from clinical samples by using reverse transcriptidase–polymerase chain reactor," *J. Clin. Microbiol.*, 30:545–551, 1992.
Morita et al., "Rapid detection of virus genome from imported dengue fever and dengue hemorrhagic fever . . . ," *J. Med. Virol.*, 44:54–58, 1994.
Morita et al., "Rapid identification of dengue virus serotypes by using polymerase chain reaction," *J. Clin. Microbiol.*, 29:2107–2110, 1991.
Pierre et al., "Identification of mosquito–borne flavivirus sequences using universal primers and reverse . . . ," *Res. Virol.*, 145:93–104, 1994.
Seah et al., "Rapid, single–step RT–PCR typing of dengue virus using five NS3 gene primers," *J. Virol. Methods*, 51:193–200, 1995.
Sudiro et al., "Rapid diagnosis of dengue viremia by reverse transcriptase–polymerase chain reaction using 3'–noncoding region universal primers," *Am. J. Trop. Med. Hyg.*, 56(4):424–429, 1997.

*Primary Examiner*—Donna Wortman
*Assistant Examiner*—Brenda G. Brumback
*Attorney, Agent, or Firm*—Fish & Richardson P.C.

[57] ABSTRACT

Specific primers that amplify a portion of the 3'-noncoding regions of dengue virus types 1, 2, 3 and 4, and a method of using these primers in a rapid reverse transcriptase-polymerase chain reaction (RT-PCR) for specific detection of dengue viruses, but not other flaviviruses, is disclosed.

18 Claims, 2 Drawing Sheets

METHODS AND REAGENTS FOR RAPID DIAGNOSIS OF DENGUE VIRUS INFECTION

STATEMENT AS TO FEDERALLY SPONSORED RESEARCH

This invention was made in part with federal funding. The government may have certain rights in the invention.

FIELD OF THE INVENTION

The invention relates to methods and reagents for detecting dengue viruses.

BACKGROUND OF THE INVENTION

Dengue virus infections are serious health problems in many areas of the world. Dengue virus can cause two forms of disease, dengue fever (DF) and dengue hemorrhagic fever (DHF). While DF is a self-limiting febrile disease, DHF can lead to life-threatening complications. Laboratory diagnosis of dengue virus infection has depended mainly upon the isolation of dengue virus using mosquito cell cultures or inoculation of mosquitos, detection of anti-dengue antibody by IgM or IgG ELISA, and/or hemagglutination inhibition (HI) assays. Isolation of dengue virus is tedious and time consuming, however, and serological testing generally requires paired serum samples obtained several days or weeks apart, which are not always available.

Polymerase chain reaction (PCR) has the potential for sensitive, specific, and rapid detection of minute quantities of certain genetic material in clinical specimens, thus providing an attractive approach for the rapid diagnosis of dengue virus infection. Several methods of reverse transcriptase (RT)-PCR using different pairs of primers for dengue viruses and different approaches for the detection of amplification products have been previously reported. However, most of the published methods require more than 24 hours for analysis. Rapid RT-PCR methods for detection of dengue viremia have been reported, but they have not been shown to detect all four dengue serotypes in clinical specimens. The objective of several of these reports was to determine the serotype of dengue virus strain with which an individual was infected. RT-PCR followed by hybridization to serotype-specific probes, or RT-PCR followed by nested PCR, have been used for this purpose. Lanciotti et al., *J. Clin. Microbiol.*, 30:545–551 (1992). Although these methods are sensitive, they still require considerable time and labor for use in patient management. Morita et al. describes a rapid and simple method using NP-40 and serotype-specific primers, in which RNA isolation, virus detection and typing can be done in a single reaction tube. Morita et al., *J. Clin. Microbiol.*, 29:2107–2110 (1991); *J. Med. Virol.*, 44:54–58 (1994).

SUMMARY OF THE INVENTION

The invention is based on the discovery that specific primers which amplify a portion of the 3'-noncoding regions of dengue virus types 1, 2, 3, and 4 can be used in a rapid reverse transcriptase-polymerase chain reaction (RT-PCR) method for specific detection of dengue viruses, but not other flaviviruses, such as West Nile virus, Japanese encephalitis virus and yellow fever virus, or the alphavirus Sindbis virus. The method enables diagnosis of dengue virus infection within six hours.

In one aspect, the invention features isolated nucleic acids having the sequences 5'-AAA CCG TGC TGC CTG TAG-3' (ALD-1, SEQ ID NO:1); 5'-AAA CTG TGC AGC CTG TAG-3' (ALD-1B, SEQ ID NO:2); 5'-AAA CCG TGC AGC CTG TAG-3' (ALD-1c, SEQ ID NO:6); and 5'-TCT CTC CCA GCG TCA ATA-3' (ALD-2, SEQ ID NO:3), which act as primers in a method of reverse transcriptase-polymerase chain reaction (RT-PCR). Each of these primers is 18 bases in length. The entire 18 nucleotide primers can be used, as well as any portion of these sequences of at least fifteen contiguous bases in length. For example, oligonucleotides of 16 nucleotides derived from ALD-2 and having the sequence 5'-TCT CTC CCA GCG TCA A-3' (SEQ ID NO:4), or 5'-T CTC CCA GCG TCA ATA-3' (SEQ ID NO:5), can be used. In addition, other oligonucleotides that are fifteen to twenty three nucleotides in length, and that overlap ALD-1, ALD-1B, ALD-1c, and ALD-2, e.g., by at least 15 nucleotides, can also be used as primers. In general, the additional nucleotides beyond the 18 nucleotides of SEQ ID NOs:1, 2, or 6 (i.e., sense primers) should corresond to nucleotide sequences located on either side of the primer sequence found in dengue virus 1, 2, 3, or 4. Additional nucleotides beyond the 18 nucleotides of SEQ ID NO:3 (e.g., antisense primers) should generally correspond to nucleotide sequences complementary to the sequence recognized by the primer in dengue virus 1, 2, 3, or 4.

In another aspect, the invention is a method of detecting dengue virus in a biological sample. The method includes the steps of incubating RNA extracted from the sample with reverse transcriptase and a first dengue virus-specific primer of, e.g., 15 to 28 nucleotides, and including at least 15 consecutive nucleotides of, e.g., SEQ ID NO:3, wherein the first dengue virus-specific primer is fully complementary to a region in the dengue viral nucleic acid complementary to SEQ ID NO:3, for a time and under conditions sufficient to allow double stranded nucleic acid to form; adding a second dengue virus-specific primer of, e.g., 15 to 28 nucleotides and including at least 15 consecutive nucleotides of, e.g., SEQ ID NO:1, wherein the second dengue virus-specific primer is identical to a region in the dengue viral nucleic acid that includes SEQ ID NO:1, and a thermostable DNA polymerase; incubating for a time and under conditions sufficient to allow said double stranded nucleic acid, if any, to be amplified by polymerase chain reaction to form reaction products; and detecting the reaction products as an indication of the presence of dengue virus in the sample.

In another method of the invention, a third dengue virus-specific primer is added along with the second primer, wherein the third primer is, e.g., 15 to 28 nucleotides in length, and includes at least 15 consecutive nucleotides of e.g., SEQ ID NO:2, wherein the second dengue virus-specific primer is identical to a region in the dengue viral nucleic acid that includes e.g., SEQ ID NO:1.

In another aspect, the invention features a kit that can be used to detect the presence of dengue virus in a sample. The kit includes a first dengue virus-specific primer of, e.g., 15 to 28 nucleotides and including at least 15 consecutive nucleotides of, e.g., SEQ ID NO:3, wherein the first dengue virus-specific primer is fully complementary to a region in the dengue viral nucleic acid complementary to SEQ ID NO:3; a second dengue virus-specific primer of, e.g., 15 to 28 nucleotides and including at least 15 consecutive nucleotides of e.g., SEQ ID NO:1, wherein the second dengue virus-specific primer is identical to a region in the dengue viral nucleic acid that includes SEQ ID NO:1; and, reagents for performing reverse-transcriptase-polymerase chain reaction (RT-PCR).

The invention also features a method of quantitating dengue virus in a sample. The method inludes the steps of mixing RNA extracted from the sample with a known quantity of competitor RNA; incubating the mixture with reverse transcriptase and a first dengue virus-specific primer of, e.g., 15 to 28 nucleotides and including at least 15 consecutive nucleotides of, e.g., SEQ ID NO:3, wherein the first dengue virus-specific primer is fully complementary to a region in the dengue viral nucleic acid complementary to SEQ ID NO:3, for a time and under conditions sufficient to allow double stranded nucleic acid to form; adding a second dengue virus-specific primer of, e.g., 15 to 28 nucleotides and including at least 15 consecutive nucleotides of, e.g., SEQ ID NO:6, wherein the second dengue virus-specific primer is identical to a region in the dengue viral nucleic acid that includes SEQ ID NO:6, and a thermostable DNA polymerase; incubating for a time and under conditions sufficient to allow said double stranded nucleic acid to be amplified by polymerase chain reaction to form reaction products; detecting the reaction products; and comparing the amount of the reaction product obtained with the amount obtained in the absence of said competitor RNA.

Another method of quantitating dengue virus has the following steps: mixing RNA extracted from the sample with a known quantity of competitor RNA; incubating the mixture with reverse transcriptase and a first dengue virus-specific primer of, e.g., 15 to 28 nucleotides and including at least 15 consecutive nucleotides of, e.g., SEQ ID NO:3, wherein the first dengue virus-specific primer is fully complementary to a region in the dengue viral nucleic acid complementary to SEQ ID NO:3, for a time and under conditions sufficient to allow double stranded nucleic acid to form; adding a second dengue virus-specific primer of, e.g., 15 to 28 nucleotides and including at least 15 consecutive nucleotides of, e.g., SEQ ID NO:6, wherein the second dengue virus-specific primer is identical to a region in the dengue viral nucleic acid that includes SEQ ID NO:6, and a thermostable DNA polymerase; incubating for a time and under conditions sufficient to allow said double stranded nucleic acid to be amplified by polymerase chain reaction to form reaction products; detecting the reaction products; and quantitating the reaction products obtained, by comparison to known amounts of competitor RNA.

The invention also includes a method of microplate reverse hybridization for determining the serotype of dengue virus in a biological sample. The method includes the steps of isolating RNA from a sample; incubating RNA extracted from the sample with reverse transcriptase and a primer, e.g., having the sequence of SEQ ID NO:3, for a time and under conditions sufficient to allow double stranded nucleic acid to form; adding primers, e.g., having the sequences of SEQ ID NO:1 and SEQ ID NO:2, a thermostable DNA polymerase, and labelled nucleotides; incubating for a time and under conditions sufficient to allow said double stranded nucleic acid, if any, to be amplified by polymerase chain reaction to form labelled reaction products; adding aliquots of labelled reaction products to separate microwells, each of which is coated with a probe specific for one of the four dengue virus serotypes, under conditions sufficient for hybridization to occur; and detecting the products of the hybridization reaction.

An "isolated nucleic acid" is a nucleic acid that is free of the nucleic acids that normally flank it in the genome. The term "nucleic acid" can encompass both RNA and DNA, and can include synthetic (e.g., chemically synthesized) nucleic acids.

Unless otherwise defined, all technical and scientific terms used herein have the same meaning as commonly understood by one of ordinary skill in the art of molecular biology. Although methods and materials similar or equivalent to those described herein can be used in the practice or testing of the present invention, suitable methods and materials are described herein. All publications, patent applications, patents, and other references mentioned herein are incorporated by reference in their entirety. In case of conflict, the present specification, including definitions, will control. In addition, the materials, methods, and examples are illustrative only and are not intended to be limiting.

Other features and advantages of the invention will be apparent from the detailed description and the claims.

DETAILED DESCRIPTION

Figure 1:
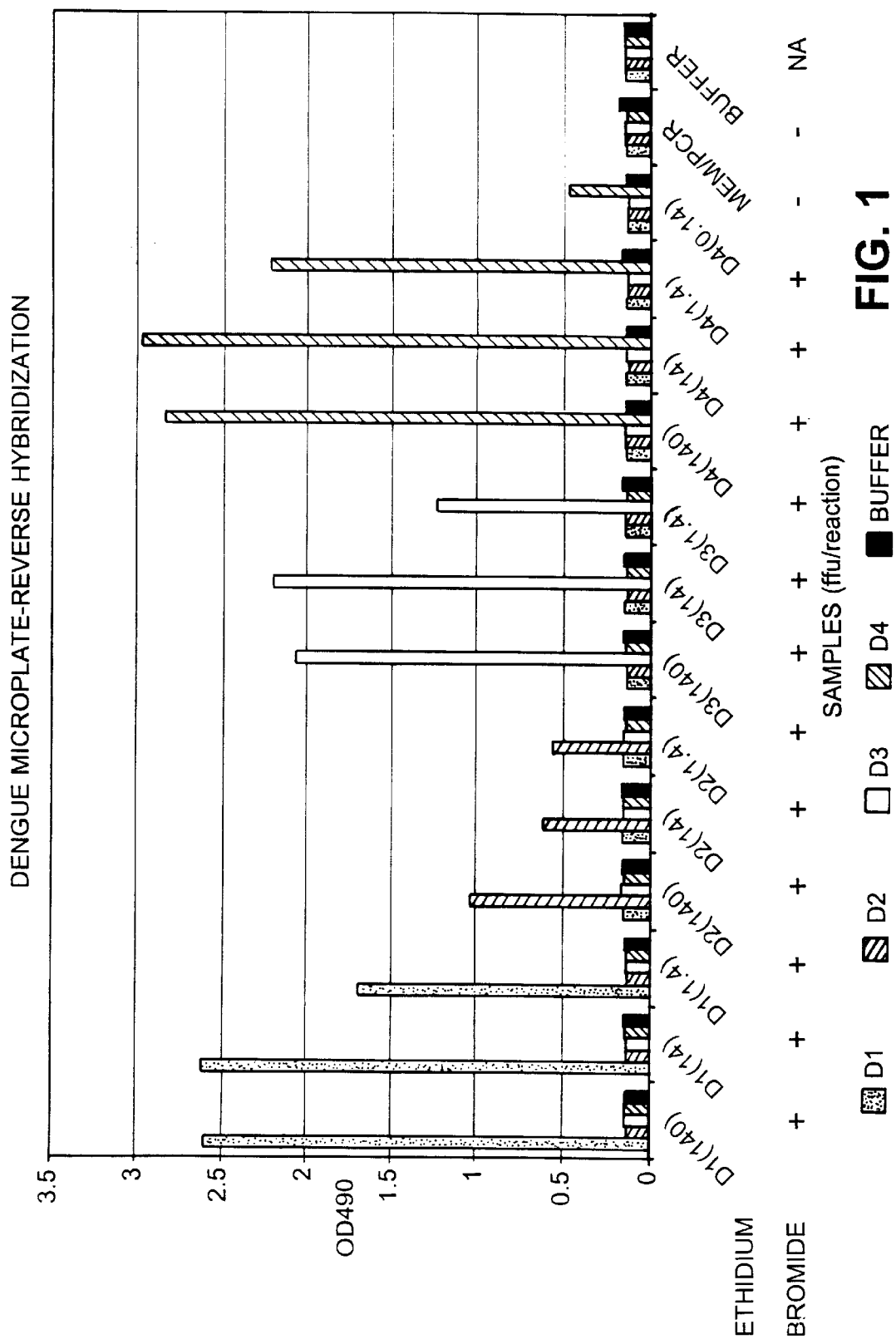
FIG. 1 is a bar graph showing the results of microplate reverse hybridization reactions of reference strains of dengue viruses to serotype-specific probes.

To detect dengue viruses in serum or plasma specimens, specific primers were designed for use in a method of reverse transcriptase-polymerase chain reaction (RT-PCR). Using these primers, all four dengue serotypes can be detected in a single reaction, thus reducing the cost and preparation time of the test. The primers are useful for specifically amplifying the 3'-noncoding region of dengue virus types 1, 2, 3, and 4, while not amplifying any regions of other flaviviruses, such as West Nile virus, Japanese encephalitis virus, yellow fever virus, or the alphavirus Sindbis virus. RT-PCR using the dengue virus-specific primers detects not only laboratory strains of dengue virus, but also dengue viruses of all four serotypes found in clinical specimens, with high sensitivity. The primers amplify a region that varies in size among the four different dengue virus serotypes. The method does not require additional steps such as hybridization to dengue virus serotype-specific probes or nested PCR following the RT-PCR reaction. Dengue virus serotypes can be determined using a microplate reverse hybridization assay that utilizes probes specific for each of the dengue virus serotypes.

The sensitivity of the RT-PCR assay using the dengue virus-specific primers was similar to that of a quantitative fluorescent focus assay used to detect dengue viruses in cell culture. Combining a silica method for RNA isolation and RT-PCR, dengue virus could be detected in six hours. In one study using this method, dengue virus was detected in 38 of 39 plasma specimens that were dengue virus-positive by the mosquito inoculation technique.

The RT-PCR method described herein was used in a second study of 117 plasma samples from 64 children with acute febrile illnesses in a dengue endemic area. Dengue viremia was detected in nineteen of twenty samples obtained on the day of clinical presentation. These samples were confirmed as positive for acute dengue infection by mosquito inoculation and antibody responses. The overall sensitivity of the method is 91.4% (32/35 positive; 95% confidence interval (CI)=82.2–100%). The results from testing plasma samples from febrile non-dengue patients showed 95.4% specificity (42/44 negative; 95% CI=89.3–100%).

Primer Design

The sequence data available for the four dengue virus serotypes is quite limited, complicating attempts to define regions common to the four dengue serotypes to which PCR primers could be targeted. The data available in the Genbank database was analyzed to design dengue virus-specific primers that recognize all four dengue virus serotypes, but not other related flaviviruses. Ideal primers would be those that exactly match sequences in all four dengue virus serotypes, since a mismatch of only a few bases between the primer and the virus can result in false negative results.

The sequences of dengue virus type 1 Singapore S275/90 strain (Genbank accession M87512), dengue virus type 2 New Guinea C strain (M29095 M19727), dengue virus type 2 Jamaica stain (M20558), dengue virus type 2 S1 vaccine strain (M19197), dengue virus type 3 H87 strain (M93130), dengue virus type 4 Caribbean 814669 strain (M14931 M17255), and the related viruses, Japanese encephalitis virus (M18370, M55506, D90195), yellow fever virus (K02749), and Kunjin virus (D00246) were compared in the 3' noncoding region of the viral genomes. The 3' noncoding region was chosen for analysis, because the coding region tends to undergo mutations in which nucleotides are altered, but the corresponding amino acid is not, due to the degeneracy of the genetic code. The 3' noncoding regions of positive strand RNA viruses may function in virus replication, and therefore these regions may be conserved among dengue viruses. It has been observed that the 3' noncoding regions of dengue viruses isolated in different epidemics and in different countries are conserved among the four dengue virus serotypes.

A highly conserved region corresponding to nucleotides 10,406 to 10,423 of dengue-1 was found in the 3' noncoding region of dengue viruses. The finding of this conserved region was surprising, as the level of mutation of positive strand RNA viruses such as dengue virus is quite high, approximately one million times faster than genomic DNA. Within this region, only two base changes in dengue-2 were found. In the other flaviviruses checked, with maximal alignment, a difference of at least 5 bases was found.

The primers chosen were 18 nucleotides long. Oligonucleotides shorter than this tend to anneal to nucleic acids nonspecifically. Longer oligonucleotides can form hairpin loops, or can dimerize, reducing the sensitivity of the assay. The sense primer used in the experiments was a mixture of a primer having a sequence homologous to dengue viruses 1, 3, and 4 (ALD-1: 5'-AAA CCG TGC TGC CTG TAG -3'; SEQ ID NO:1), and a primer having a sequence homologous to dengue-2 (ALD-1b: 5'-AAA CTG TGC AGC CTG TAG-3'; SEQ ID NO:2) (Table 1). The antisense primer had a sequence complementary to nucleotides 10,617 to 10,634 of dengue-1 (ALD-2: 5'-TCT CTC CCA GCG TCA ATA-3'; SEQ ID NO:3) (Table 1); this sequence is identical to that found in dengue-3. Dengue-2 and 4 each have a single base difference from this sequence in the corresponding region of the genome. In Japanese encephalitis virus and yellow fever virus, there are four and three base mismatches, respectively. Use of this combination of primers allowed detection of all four dengue virus serotypes. When ALD-1 and ALD-2 alone were used in the assay, dengue virus 1, 3, and 4 were all detected, but sensitivity for dengue-2 was approximately ten times less than when ALD-1, ALD-1b, and ALD-2 were used. Table 2 shows the sequence for 5 nucleotides in the 5' and 3' direction for each of the primers used herein, in various reference strains of dengue virus.

TABLE 1

Primer Sequences

| Sense Primers | | | | | | | SEQ ID NO. |
|---|---|---|---|---|---|---|---|
| ALD-1 | 5' - AAA | CCG | TGC | TGC | CTG | TAG - 3' | 1 |
| ALD-1b | 5' - AAA | CTG | TGC | AGC | CTG | TAG - 3' | 2 |
| nucleotide position in dengue virus genome: | 10,406 | | | | | 10,423 | |
| DEN-1 | 5' - AAA | CCG | TGC | TGC | CTG | TAG - 3' | 1 |
| DEN-2 | 5' - ■■■ | ■T■ | ■■■ | A■■ | ■■■ | ■■■ - 3' | 2 |
| DEN-3 | 5' - ■■■ | ■■■ | ■■■ | ■■■ | ■■■ | ■■■ - 3' | 1 |
| DEN-4 | 5' - ■■■ | ■■■ | ■■■ | ■■■ | ■■■ | ■■■ - 3' | 1 |
| Antisense primer | | | | | | | |
| ALD-2 | 5' - TCT | CTC | CCA | GCG | TCA | ATA - 3' | 3 |
| nucleotide position in dengue virus genome: | 10,617 | | | | | 10,634 | |
| DEN-1 | 5' - TCT | CTC | CCA | GCG | TCA | ATA - 3' | 3 |
| DEN-2 | 5' - ■■■ | ■T■ | ■■■ | ■■■ | ■■■ | ■■■ - 3' | 3 |
| DEN-3 | 5' - ■■■ | ■■■ | ■■■ | ■■■ | ■■■ | ■■■ - 3' | 3 |
| DEN-4 | 5' - ■■■ | T■■ | ■■■ | ■■■ | ■■■ | ■■■ - 3' | 8 |

*Boxes indicate sequence identity to the nucleotide above

TABLE 2

Extended Sequences for Primers

| | | SEQ ID NO. |
|---|---|---|
| ALD-1 (sense) | : 5' - AAA CCG TGC TGC CTG TAG - 3' | 1 |
| Den-1/Singapore S275/90: | : TG AGC ■■■ ■■■ ■■■ ■■■ ■■■ ■■■ CTT CA (nucleotide 10,401 to 10,428) | 9 |
| Den-3/H87 | : TG AGC ■■■ ■■■ ■■■ ■■■ ■■■ ■■■ CTC CG (nucleotide 10,387 to 10,409) | 10 |
| Den-4/Caribbean 814669 | : TG AGC ■■■ ■■■ ■■■ ■■■ ■■■ ■■■ CTC CG (nucleotide 10,317 to 10,444) | 10 |

TABLE 2-continued

Extended Sequences for Primers

| | | | | SEQ ID NO. |
|---|---|---|---|---|
| ALD-1b (sense) | : | 5' - AAA CTG TGC AGC CTG TAG - 3' | | 2 |
| Den-2/New Guinea C | : TG AGT ■■■ ■■■ ■■■ ■■■ ■■■ ■■■ CTC | CA (nucleotide 10,403 to 10,430) | | 11 |
| Den-2/SI vaccine | : TG AGC ■■■ ■■■ ■■■ ■■■ ■■■ ■■■ CTC | AC (nucleotide 10,384 to 10,411) | | 12 |
| Den-2/Jamaica | : TG AGT ■■■ ■■■ ■■■ ■■■ ■■■ ■■■ CTC | CA (nucleotide 10,403 to 10,430) | | 11 |
| ALD-1c (sense) | 5' - AAA CCG TGC AGC CTG TAG - 3' | | | 6 |
| [The nucleotide sequences flanking the ALD-1c primer are the same as for ALD-1 and ALD-1b, above] | | | | |
| ALD-2 (antisense) | 5' - TCT CTC CCA GCG TCA ATA - 3' | | | 3 |
| Den-1/Singapore S275/90 | : TC TGG ■■■ ■■■ ■■■ ■■■ ■■■ ■■■ TGC | TG (nucleotide 10,162 to 10,639) | | 13 |
| Den-2/New Guinea C | : TC TGG ■■■ T■■ ■■■ ■■■ ■■■ ■■■ TGC | TG (nucleotide 10,618 to 10,645) | | 14 |
| Den-2/S1 vaccine strain | : TC TGG ■■■ T■■ ■■■ ■■■ ■■■ ■■■ TGC | TG (nucleotide 10,598 to 10,625) | | 14 |
| Den-2/Jamaica | : TC TGG ■■■ T■■ ■■■ ■■■ ■■■ ■■■ TGC | TG (nucleotide 10,618 to 10,645) | | 14 |
| Den-3/H87 | : TC TGG ■■■ C■■ ■■■ ■■■ ■■■ ■■■ TGC | TG (nucleotide 10,591 to 10,618) | | 7 |
| Den-4/Caribbean 814669 | : TC TGG ■■■ T■■ ■■■ ■■■ ■■■ ■■■ TGC | TG (nucleotide 10,539 to 10,566) | | 14 |

*Boxes indicate sequence identity to the nucleotide above.

Despite the highly conserved nature of the primers used in these experiments, the sequences in the region between the primers are quite variable among the different dengue serotypes. The locations of the primers and the regions between them, in nucleotides, for the dengue virus strains used in these experiments, are shown in Table 3. The sequence identity of the PCR products among the four serotypes of dengue virus ranges between 77% and 90%. The expected sizes of the PCR products are 229 bp, 233 bp, 227 bp, and 241 bp for dengue virus types 1, 2, 3, and 4, respectively. The difference in sizes of the PCR products allows the four dengue serotypes to be distinguished from one another by agarose gel electrophoresis and ethidium bromide staining. Additionally, since the region between the primers varies substantially among the four dengue serotypes, the PCR products can be distinguished by sequencing or by hybridization to probes specific for each serotype. The PCR products produced in this assay are relatively small, and thus the PCR reaction time is correspondingly short.

TABLE 3

| Primer | Virus Strain | Location of Primer (nucleotides) | Regions between primer sequences |
|---|---|---|---|
| ALD-1 | Den-1/Singapore S275/90 | 10,406–10,423 | 10,424–10,616 |
| | Den-3/H87 | 10,387–10,404 | 10,405–10,595 |
| | Den-4/Caribbean 814669 | 10,322–10,339 | 10,340–10,543 |
| ALD-1b | Den-2/New Guinea G | 10,408–10,425 | 10,426–10,622 |
| | Den-2/Jamaica | 10,408–10,425 | 10,426–10,622 |
| | Den-2/S1 vaccine strain | 10,389–10,406 | 10,407–10,602 |
| ALD-2 | Den-1/Singapore S275/90 | 10,617–10,634 | 10,424–10,616 |
| | Den-2/New Guinea G | 10,623–10,640 | 10,426–10,622 |
| | Den-2/Jamaica | 10,623–10,640 | 10,462–10,622 |
| | Den-2/S1 vaccine strain | 10,603–10,620 | 10,407–10,602 |
| | Den-3/H87 | 10,596–10,613 | 10,405–10,595 |
| | Den-4 Caribbean 814669 | 10,544–10,561 | 10,340–10,543 |

It is often difficult to clinically identify children with dengue until defervescence. The diagnostic assays described herein will be helpful in the rapid identification of patients with dengue virus, and early management of patients with dengue virus infections.

EXAMPLES

Example 1

Sensitivity and Specificity of RT-PCR Using Dengue Virus-Specific Primers

The sensitivity of the RT-PCR assay using dengue virus-specific primers in detecting dengue virus was determined by comparison to results obtained using the immunofluorescent focus assay. Normal human serum (Human AB serum, Advanced Biotechnologies Inc., Columbia, Mass.) spiked with ten-fold serial dilutions of reference virus stocks was subjected to RT-PCR using the dengue virus specific primers. The following reference virus strains were used: dengue virus type 1 Hawaii strain, dengue virus type 2 New Guinea C strain, dengue virus type 3 CH53489 strain, and dengue virus type 4 814669. Virus stocks were titered by fluorescent focus assay in CV-1 cells, as described previously. Kontny et al., *J. Virol.*, 62:3928–3933 (1988). Briefly, cells were infected with serially diluted virus in 8-chamber slides. After incubation for 20 hours at 37° C., the slides were fixed and stained by indirect immunofluorescence using mouse anti-dengue hyperimmune ascites fluid and fluorescein isothiocyanate (FITC)-conjugated sheep anti-mouse IgG, and infected cells were counted. The sensitivity of this method is comparable to plaque assay in CV-1 cells.

RNA was isolated from each virus-spiked serum sample by a modification of a so-called "silica" method described by Boom et al. and later applied to isolation of dengue virus RNA. Boom et al., *J. Clin. Microbiol.*, 28:495–503 (1990); Chan et al., *J. Virol. Methods*, 49:315–322 (1994); Chungue et al., *J. Med. Virol.*, 40:142–145 (1993); Seah et al., *J. Virol Methods*, 51:193–200 (1995). In brief, 20 $\mu$l of sample was vortexed for five seconds with 180 $\mu$l of lysing buffer (4M guanidine isothiocyanate, 40 mM Tris-HCl pH 6.4, 17 mM EDTA pH 8.0, 1% Triton X-100) and 8 μl of acid-treated, size-fractionated silica particles (Sigma chemicals, St. Louis, Mo.), then allowed to stand at room temperature for 10 minutes, mixed again, and centrifuged at 13,000×g for 15 seconds. The silica pellet was washed twice in 200 μl washing buffer (50% ethanol, 10 mM Tris-HCl pH 7.4, 1 mM EDTA, and 50 mM NaCl), and finally rinsed in 100 μl of DEPC water. The pellet was resuspended in 15 μl of water containing 2.5 U of RNase inhibitor (Pharmacia, Piscataway, N.J.) and incubated at 56° C. for 7 minutes. After centrifugation at 13,000×g for 2 minutes, 14 μl of RNA sample was collected.

RNA isolated from the virus-spiked serum samples was then subjected to RT-PCR using the dengue-virus specific probes. The RT-PCR method consists of reverse transcription using the downstream primer ALD-2, heat inactivation of the reverse transcriptase, and PCR incorporating the upstream primers ALD-1 and ALD-1b. RNA (14 μl) was added to 6 μl of RT-mix solution containing 50 mM KCl, 10 mM Tris-HCl (pH 9.0 at 25° C.), 0.1% Triton X-100, 1.0 mM $MgCl_2$, 25 pmol of downstream primer ALD-2, 0.2 mM of each dNTP, 2.0 U of AMV reverse transcriptase (Promega, Madison, Wis.), and 4.0 U of RNase inhibitor (Pharmacia). Reverse transcription was carried out at 42° C. for 30 minutes, followed by inactivation of the reverse transcriptase at 95° C. for 5 minutes. PCR-mix (30 μl) was then added to the reaction mixture. PCR-mix contains 50 mM KCl, 10 mM Tris-HCl (pH 9.0 at 25° C.), 0.1% Triton X-100, 1.0 mM $MgCl_2$, 25 pmol of each upstream primer ALD-1 and ALD-1b, 0.2 mM of each of the dNTPs, and 1.25 U of Tth DNA polymerase (Promega). The reaction was carried out at 92° C. for 1 minute, 53° C. for 1 minute and 72° C. for 1 minute, for 10 cycles; 92° C. for 30 seconds, 55° C. for 30 seconds, 72° C. for 30 seconds, for 30 cycles; followed by incubation at 72° C. for 5 minutes. Water used to elute the RNA, or human AB serum, were used as negative controls. Samples (15 μl) were subjected to electrophoresis in 2.2% agarose gels. The gels were then stained with ethidium bromide. Precautions were taken to avoid carryover contamination, including the use of several samples without RNA as controls in each run, physical separation of pre- and post-PCR manipulations, and the use of aerosol-barrier pipettes.

As determined from the gels, the sensitivity of the RT-PCR using the dengue virus-specific primers is at least 2 FFU/20 μl sample for dengue viruses 1, 3 and 4; and 20 FFU/20 μl sample for dengue-2. Other than the bands of expected size, there was a minor faint band that migrated faster than the major band in samples containing dengue-1, dengue-2, and dengue-4. This minor band decreased in intensity in parallel to the intensity of the major band in serial dilutions of virus as well as by increasing the annealing temperature, and was not present in negative serum controls. Secondary structure of the 3'-noncoding region products may be responsible for this band.

RT-PCR using the dengue virus-specific primers of the invention also gave positive results with other laboratory strains of dengue viruses tested, including dengue virus type 1 Mochizuki strain, dengue virus type 2 strains Thai-257 and M11355, dengue virus type 3 strains Sri Lanka-904 and Sri Lanka-969, and dengue virus type 4 strains H241 and Thai-286. Results were negative for flaviviruses other than dengue virus, such as West Nile virus, yellow fever virus, Japanese encephalitis virus, and Sindbis virus.

Example 2

Study of Plasma Specimens From Children With Acute Dengue Infection

To confirm that the new dengue virus-specific probes worked equally well with clinical samples as with virus-spiked serum samples, the RT-PCR method described above was applied to 39 plasma samples from children with dengue fever or dengue hemorrhagic fever. Blood samples were obtained from children enrolled in a prospective study of dengue infections at the Children's Hospital, Bangkok, Thailand, and the Kamphaeng Phet Provincial Hospital, Kamphaeng Phet, Thailand, in 1994. Children with fever of 72 hours or less in duration and facial flushing without obvious cause were eligible to participate in the study. Blood was drawn daily until 1 day after defervescence, or up to 5 days, and then at convalescence (8 to 10 days after enrollment). Blood was collected into EDTA-containing tubes; plasma was separated and stored at -70° C. until RT-PCR was performed.

Dengue IgM and IgG ELISA and hemagglutination inhibition assays were performed on each of the samples by methods that have been described previously in Innis et al., Am. J. Trop. Med. Hyg., 40:418–427 (1989). Dengue virus isolation was attempted by mosquito inoculation for the first three consecutive days, or until virus isolation was negative on subsequent days tested, by methods that have been described previously. Rosen et al., Am. J. Trop. Med. Hyg., 23:1153–1160 (1974). A child was diagnosed as having acute dengue infection when the serological tests were positive, and/or dengue virus could be isolated. Control specimens used in this study were from children having febrile illness, but no evidence of acute dengue infection by serological or mosquito inoculation tests with appropriately timed specimens.

The results of the study are shown in Table 4. In these experiments, the samples were all believed to be positive, as dengue virus had previously been isolated from them by mosquito inoculation. Six samples containing dengue-1, eleven samples containing dengue-2, six samples containing dengue-3, and sixteen samples containing dengue-4 were tested. All the samples had been obtained on the day of clinic presentation, no more than 72 hours after the onset of fever, and from zero to five days before defervescence.

Results of the RT-PCR analysis are shown in Table 4 by day relative to defervescence (defervescence is defined as day 0). Thirty eight of the thirty-nine samples which had been positive by mosquito inoculation were found to be positive by RT-PCR. The one specimen that was positive by mosquito inoculation, but negative by RT-PCR using the dengue virus-specific primers, was obtained from a dengue-2 virus-infected patient on the last day of fever. The controls, two samples from healthy persons, and one sample from a patient with hepatitis-C, were negative for dengue virus by RT-PCR.

TABLE 4

Comparison to RT-PCR to mosquito inoculation for dengue virus detection in plasma specimens (preliminary study)
Day that samples were obtained relative to defervescence*

| Dengue Serotype | Total | -5 | -4 | -3 | -2 | -1 | 0 | unknown+ |
|---|---|---|---|---|---|---|---|---|
| Dengue-1 | 6/6 | — | 2/2 | 1/1 | 2/2 | 1/1 | | — |
| Dengue-2 | 10/11 | 1/1 | 2/2 | 3/3 | 2/2 | 2/2 | 0/1 | — |
| Dengue-3 | 6/6 | — | — | 2/2 | 2/2 | 1/1 | — | 1/1 |
| Dengue-4 | 16/16 | — | — | 4/4 | 8/8 | 4/4 | — | — |
| Total | 38/39 | 1/1 | 4/4 | 10/10 | 14/14 | 8/8 | 0/1 | 1/1 |

*The day when the body temperature fell and remained below 38° C. is defined as day zero.
+Subject withdrawn from study before defervescence.

The results of this study show that the RT-PCR method using dengue-virus specific primers described herein can rapidly indicate whether an acutely febrile patient is infected with dengue virus, which is critical for patient management. In these experiments, the method was applied to plasma specimens obtained on the day of presentation to the outpatient clinic, no more than 72 hours after the onset of fever.

Example 3

Comparison of Dengue Virus Detection by RT-PCR or Mosquito Inoculation

To further analyze the sensitivity and specificity of the RT-PCR method described herein to the mosquito inoculation method, plasma specimens from twenty children known to have dengue viremia, five children each being infected with one of the four dengue serotypes, were tested. For each child, the plasma sample obtained at presentation (study day one), the last daily plasma sample that yielded dengue virus by mosquito inoculation (last mosquito inoculation positive; Last MI+), the plasma sample from the next daily bleed (first mosquito inoculation negative; First MI−), and the convalescent sample (Follow up), were studied. In most cases, mosquito inoculation was not performed on follow up plasma specimens because a previous blood specimen was negative for viremia, and it was assumed that later samples would have been negative if tested. A total of 73 samples from the twenty children were tested. In some cases, the last mosquito inoculation positive sample was the same as the study day one sample, or no blood sample was obtained on the day after the last mosquito inoculation positive sample.

Random plasma samples obtained at enrollment from 44 study subjects who had no serological evidence of dengue infection and whose blood samples were negative for dengue viremia by mosquito inoculation were used as controls. Specimens were tested by RT-PCR under code. Thus, a total of 117 samples (73 DV and 44 control) from 64 children were tested.

Table 5, below, shows the results obtained with RT-PCR using dengue virus-specific primers, compared to results obtained within the mosquito inoculation assay. RT-PCR was performed as described in Example 2, supra. Mosquito inoculation was performed by the method described by Rosen and Gubler, *Am. J. Trop. Med. Hyg.*, 23:1153–1160 (1974). In brief, undiluted plasma was inoculated into adult *Toxorhynchites splendens*, 0.34 µl per mosquito, 20 mosquitos per specimen. Mosquitoes were incubated at 30° C. for 12–14 days. Infected mosquitoes were detected by fluorescent antibody (FA) staining of head squashes using polyvalent anti-dengue mouse ascitic fluid and anti-mouse IgG-FITC. All mosquito bodies from specimens that yielded at least one FA-positive head were triturated in media plus 10% FCS; triturates were passaged one or more times in T-25 flasks of C6/36 cells for seven days. Culture supernatants were assayed with virus-specific Mabs [flavivirus group (4G2), dengue complex (2H2), dengue-1 (1F1), dengue-2 (3H5), dengue-3 (10C10), dengue-4 (1H10), Japanese encephalitis virus (J93)] in an antigen-capture ELISA. Kuno et al., *J. Virol. Meth.*, 12:93–103 (1988).

Of 73 clinical samples tested, 35 were positive for dengue virus by mosquito inoculation, while 38 were positive for dengue virus by RT-PCR using the dengue-specific primers. Thirty-two of the 38 RT-PCR positive samples were also positive by mosquito inoculation. Three of 35 samples positive by mosquito inoculation were negative by RT-PCR. Among 44 samples from the febrile non-dengue control group, two samples were positive by RT-PCR. Thus, the overall sensitivity of the method is 91.4% (32/35 positive; 95% confidence interval (CI)=82.2–100%). The results from testing plasma samples from febrile non-dengue children showed 95.4% specificity (42/44 negative; 95% CI=89.3–100%).

TABLE 5

Comparison of RT-PCR and mosquito inoculation for detection of dengue viremia during acute febrile illness

|  | Dengue[+] | | Nondengue[++] |
| --- | --- | --- | --- |
|  | Virus Isolation positive | Virus Isolation negative | Virus Isolation negative |
| RT-PCR positive | 32 | 6* | 2** |
| RT-PCR negative | 3 | 32 | 42 |
| Total | 35 | 38 | 44 |

[+]Acute febrile dengue virus infection confirmed by mosquito inoculation and serological tests.
[++]Acute febrile illness without evidence of acute dengue infection by mosquito inoculation and complete serological testing.
*Five of these showed weak bands and were negative on repeat testing.
**Both showed weak bands and were negative on repeat testing.

Samples obtained late in the course of acute dengue infection that were positive by RT-PCR but negative by mosquito inoculation showed weak bands, and five of six such samples were RT-PCR negative on repeat testing. This result agrees with the observations that samples for either virus isolation or RT-PCR should ideally be obtained in the early phase of illness. Gubler et al., *Bull. World Health Organ.*, 59:623–630 (1981); Chan et al., *J. Virol Methods*, 49:315–322 (1994). The findings described herein may reflect a low virus titer in the plasma in the later stages of illness. The presence of dengue virus at low titer in patient serum has been reported as late as twelve days after the onset of illness using the mosquito inoculation technique. Gubler et al., supra.

Tables 6 and 7, below, show RT-PCR results for samples from the twenty children with dengue viremia with reference to the time of sample collection. As shown in Table 6, dengue virus was detected in nineteen of twenty samples obtained on the day of presentation by the RT-PCR method using the dengue virus-specific primers.

TABLE 6

RT-PCR Positivity of plasma from patients infected with dengue virus

| | Sample (PCR+/No. tested) | | | |
| --- | --- | --- | --- | --- |
| Virus | Day 1 | Last MI+* | First MI-** | Follow up |
| Dengue-1 | 5/5 | 4/5 | 0/5 | 1.5 |
| Dengue-2 | 4/5 | 4/5[+] | 0/4 | 2/5 |
| Dengue-3 | 5/5 | 4/5[+] | 2/4 | 0/4 |
| Dengue-4 | 5/5 | 5/5[+] | 1/5 | 0/5 |
| Total | 19/20 | 17/20 | 3/18 | 3/19 |

*The last daily plasma sample that yielded dengue virus by mosquito inoculation.
**The first daily plasma sample that was negative for dengue virus by mosquito inoculation.
[+]One of these samples was a first day sample.

The one negative sample on day 1 in Table 6 was obtained from a dengue-2 infected patient, two days before defervescence. As shown in Table 6, above, dengue viremia was detected by RT-PCR in seventeen of twenty samples obtained on the last day that yielded dengue virus by mosquito inoculation (last MI+; from three days before to one day after defervescence), but dengue RNA was not detected in one sample each of dengue-1, dengue-2 and dengue-3. Of the eighteen first mosquito inoculation negative (First MI−) samples (obtained between two days before and one day after defervescence), dengue virus was detected in two samples that had been negative by mosquito inoculation for dengue-3, and in one sample that had been negative by mosquito inoculation for dengue-4. Of nineteen follow-up samples, dengue virus was detected by RT-PCR in one sample obtained four days after defervescence from a dengue-1 infected patient, and in two dengue-2 samples that were obtained five and seven days after defervescence. Results from these samples showed weak bands. Mosquito inoculation assays were not performed on these specimens.

A comparison of the results obtained using mosquito inoculation or RT-PCR to detect dengue virus over the course of illness using dengue virus-specific primers is shown in Table 7, below.

TABLE 7

Detection of dengue virus by mosquito inoculation and RT-PCR during the course of illness*

| Fever day+ | Total | | Dengue 1 | | Dengue 2 | | Dengue 3 | | Dengue 4 | |
|---|---|---|---|---|---|---|---|---|---|---|
| | MI+ | PCR+ | MI+ | PCR+ | MI+ | PCR+ | MI+ | PCR+ | MI+ | PCR+ |
| −7 to −4 | 2/2 | 2/2 | 2/2 | 2/2 | — | — | — | — | — | — |
| −3 to −1 | 25/30 | 24/30 | 6/7 | 6/7 | 7/8 | 6/8 | 4/5 | 4/5 | 8/10 | 8/10 |
| 0 | 5/14 | 4/14 | 2/5 | 1/5 | 1/3 | 1/3 | 2/2 | 1/2 | 0/4 | 1/4 |
| 1 to 3 | 1/7 | 2/7 | 0/2 | 0/2 | 1/2 | 1/2 | 0/2 | 1/2 | 0/1 | 0/1 |
| 4 to 8 | 0/17 | 3/17 | 0/4 | 1/4 | 0/5 | 2/5 | 0/4 | 0/4 | 0/4 | 0/4 |
| Unknown | 2/3 | 3/3 | — | — | — | — | 2/3 | 3/3 | — | — |
| TOTAL | 35/73 | 38/73 | 10/20 | 10/20 | 9/18 | 10/18 | 8/16 | 9/16 | 8/19 | 9/19 |

*number of samples positive/number tested
+relative to day of defervescence

RT-PCR was repeated on samples that gave discordant results between RT-PCR and mosquito inoculation. Two follow-up samples (both dengue-2), two first mosquito inoculation negative samples (both dengue-3), one last mosquito inoculation positive sample, and two samples from the control group which were positive by RT-PCR on the first test, were negative on repeat testing. One dengue-3 sample that was negative in the first RT-PCR and positive for mosquito inoculation gave a positive result on the second test.

Thus, on days −3 to −1, 24 of 25 samples that were positive for dengue virus by mosquito inoculation were also positive by the rapid PCR technique described herein. This RT-PCR method can therefore be used to identify, with a high degree of accuracy, children who are infected with dengue virus at an early stage of infection, allowing early intervention in the disease process.

In serial plasma specimens obtained from children with acute febrile illness, RT-PCR detected dengue virus in 34.2% of samples, while mosquito inoculation detected dengue virus in 29.9%. The overall sensitivity of the RT-PCR using dengue virus-specific primers is 91.4% (32/35; 95% CI=82.2–100%). For the samples obtained at the time of clinical presentation, which are the most important for clinical use, this method showed 95.0% sensitivity (19/20; 95% CI=85.5–100%). All first day samples that were positive by both the RT-PCR and mosquito inoculation assays, and fifteen of the seventeen later specimens which were positive by both of these assays (see Table 6), showed strong, distinctive bands. In contrast, false positive RT-PCR specimens were seen as weak bands, and the results were negative on repeat testing.

Example 4

Testing of Patient Samples for Dengue Virus Infection by RT-PCR

A blood sample is obtained from a patient suspected of being infected with dengue virus. Plasma is separated from the blood sample, and RNA is extracted from the plasma. The RNA is then subjected to RT-PCR using the dengue virus-specific primers described herein. Isolated RNA (14 $\mu$l) is added to 6 $\mu$l of RT-mix, including primer ALD-2 and reverse transcriptase. The reaction is carried out at 42° C. for 30 minutes, and the reverse transcriptase is inactivated. PCR mix, including the primers ALD-1 and ALD-1b and DNA polymerase, is then added to the reaction mixture. The reaction is carried out at 92° C. for one minute, 53° C. for one minutes, and 72° C. for one minutes, for ten cycles; 92° C. for thirty seconds, 55° C. for thirty seconds, 72° C. for thirty seconds, for thirty cycles; and 72° C. for five minutes. Aliquots of each sample are then subjected to electrophoresis in 2.2% agarose gels, and the gels are stained with ethidium bromide to detect RT-PCR products corresponding to dengue virus serotypes 1, 2, 3 or 4.

Example 5

Quantitative Competitive RT-PCR (QC RT-PCR) to Determine the Amount of Virus in Patient Samples It has been shown that high titers of dengue 2 virus in early secondary dengue virus infections correlates closely with the magnitude of the pleural effusion, a measure of plasma leakage, in DHF patients. Vaughn et al., abstract No. 125, 45th Annual Meeting of the American Society of Tropical Medicine and Hygiene, Baltimore, Md. (December, 1996). The amount of virus carried by an infected individual may therefore affect the pathogenesis of dengue fever (DF) and dengue hemorrhagic fever (DHF) patients. Viral burden has been shown to affect the outcome of disease for conditions associated with other viruses. In a study of 209 patients infected with human immunodeficiency virus-type 1 (HIV-1), the risk of acquired immunodeficiency syndrome (AIDS) and death was directly related to the plasma viral load at study entry, even among HIV-infected individuals with normal numbers of CD4+ cells. Mellors, et al., *Science* 272:1167–1170 (1996). In addition, quantitation of hepatitis C virus (HCV) RNA in plasma samples taken from HCV-infected patients has been useful in monitoring the patient response to interferon therapy. Hino et al., *Digestive Diseases and Sciences* 40:14–10 (1995).

Since viral burden may well relate to the course of the dengue virus associated diseases DF and DHF, an assay was designed to quantitate dengue virus RNA in plasma samples. The blood samples described in Example 2, supra, obtained from children enrolled in a prospective study of dengue infections, were used in this assay. Children with fever of 72 hours or less duration and facial flushing without obvious cause were eligible to participate in the study. Samples obtained at the day of presentation in the clinic were used in these experiments. Blood was collected into EDTA-containing tubes, and plasma was separated and stored at −70° C. until the RT-PCR was performed. A competitive reverse transcriptase-polymerase chain reaction (RT-PCR) was used to detect the presence of dengue virus in patient samples. This quantitative competitive RT-PCR (QC RT-PCR) method is a modification of the RT-PCR described in Example 1, supra. ALD-2 (SEQ ID NO:3) serves as an antisense primer. ALD-1c (5'-AAA CCG TGC AGC CTG TAG-3'; SEQ ID NO:6), which differs from the nucleotide sequences of ALD-1 and ALD-1b by one base, serves as the sense primer. ALD-1c detects dengue virus with the same sensitivity as the mixture of ALD-1 and ALD-1b described in Example 1, supra.

A competitive RNA template was used in this assay to quantitate the amounts of dengue viral RNA in patient samples. The competitor RNA was constructed as follows. A 233 bp PCR product of dengue-2 virus, which had been amplified by PCR using ALD-1c and ALD-2 as primers, was cloned into the pCRII vector (Invitrogen, San Diego, Calif.), resulting in plasmid pD2C. A 190 bp fragment, corresponding to nucleotides 1562 to 1751 of the religated pCRII vector cut with Bsp1286I, was then inserted into the ApaI site of the dengue-2 insert in pD2C. This construct was translated in vitro to obtain competitor RNA. A 423 bp PCR product is obtained on amplification of the competitor RNA by primers ALD-1c and ALD-2.

Dengue virus RNA levels in plasma samples were quantitated as follows. ALD-1c and ALD-2 were used as primers to amplify RNA from a 10 μl sample, in parallel with a 10 μl sample mixed with $10^4$ copies of the competitor RNA. The PCR products obtained upon amplification of wild type dengue RNA using these primers were 229 bp, 233 bp, 227 bp, and 241 bp for dengue virus type 1, 2, 3, and 4, respectively, while the product of the competitor was 423 bp, as detected by agarose gel electrophoresis and ethidium bromide staining.

This method detects as few as 100 copies of dengue virus RNA per reaction. In dengue RNA positive samples, the amount of virus is estimated by comparing the intensity of the bands of the samples in the presence and/or the absence of competitor RNA. Such estimates are useful for rapid quantitation of dengue virus in a sample. If more accurate determinations of the amount of virus are necessary, the gels can be Southern blotted and hybridized to dengue virus-specific probes, and the blots subjected to scanning densitometry.

For finer quantitation, RNA from plasma samples was mixed with known concentrations of dengue competitor RNA (250, 500, 1000, and 5000 copies for RNA level less than $10^4$ copies/10 μl; and $10^3$, $10^4$, $10^5$, and $10^6$ copies for RNA level above $10^4$ copies/10 μl or more), and RT-PCR was performed as described above. The amount of dengue RNA in the sample was determined by comparing the density of the products on the gel of PCR reactions of competitor RNA, with the density of the products of PCR reactions of the patient plasma sample.

Quantitative competitive RT-PCR (QC RT-PCR) was performed on plasma samples taken from 24 patients who were infected with dengue virus, as shown by mosquito inoculation. The results are shown in Table 8.

TABLE 8

Dengue-RNA level in patient plasma samples

| Dengue serotype | Clinical manifestation | Number of samples | Number of copies of dengue virus RNA/ml plasma |
|---|---|---|---|
| Dengue-1 | DF | 2 | $10^8$ and $10^8$–$10^9$ |
| | DHF | 4 | $>10^6$–$10^9$ |
| Dengue-2 | DF | 3 | $<5000$ – $10^5$ |
| | DHF | 1 | $10^8$ |
| Dengue-3 | DF | 1 | $10^8$ |
| | DHF | 3 | $10^7$–$10^8$ |
| Dengue-4 | DF | 5 | $>10^6$–$10^8$ |
| | DHF | 5 | $>10^6$–$10^9$ |

Categorization of the disease as DF or DHF was based on the criteria established by the WHO. This assay can be used to quantitate the level of virus in patients infected with DF and DHF.

Example 6

Microplate Reverse Hybridization to Determine Dengue Virus Serotype

A microplate-reverse hybridization method was used to determine the serotypes of dengue viruses in patient plasma specimens. In this method, digoxigenin-labeled PCR products are hybridized under stringent conditions to serotype-specific dengue virus probes immobilized on microplates. Hybridization of the labelled PCR products to the serotype-specific probes is then detected using a colorimetric assay.

The serotype-specific probes used were PCR products of portions of the 3'-noncoding regions of dengue viruses 1 to 4. ALD-1, ALD-1b, and ALD-2 were used as primers to amplify the 3' noncoding region in individual known samples of dengue virus, one for each of the four serotypes. In particular, the amplified regions were the regions between the primer sequences described in Table 3, each approximately 190 to 200 nucleotides in length. Each PCR product was cloned into the pCRII vector (Invitrogen, San Diego, Calif.), to produce the four different serotype-specific probes. The PCR product can be cut out of the vector, or the vector plus insert can to be used as a probe. Different specific probes can be made using this same technique, and the PCR product can be smaller, down to 15 nucleotides, than the probes containing the full region between the primer sequences as described in Table 3 (as long as there at least 3 to 5 differences in nucleotides between the target dengue serotype and the other three serotypes).

The four different probes were coated onto microplates using previously described methods. Inouye et al., *J. Clinical Microbiology* 28:1469–1472 (1990). Briefly, 400 ng of each of the serotype-specific probes, diluted in 0.1 ml immobilization buffer (10 mM sodium phosphate (pH 7.0), 10 mM EDTA (pH 8.0) and 1.5M sodium chloride), was denatured at 95° C. for 7 minutes. Probes specific for dengue 1, 2, 3, or 4 were then added to duplicate wells of a Maxisorp microplate (Nunc, Roskilde, Denmark). After incubation at 37° C. for 2 hours, the plates were washed with phosphate-buffered saline containing 0.05% Tween 20 (PBST) six times using an automatic plate washer. Coated plates could be stored at 4° C. for up to a month before use.

RNA was isolated and RT-PCR performed as described in Example 1, supra, except that digoxigenin-labeled dUTP was included in amplification reaction to label the PCR products. RNA was reverse transcribed using ALD-2 (SEQ ID NO:3) as the primer. Fourteen µl of isolated RNA was added to 6 µl of RT-mix solution containing 50 mM KCl, 10 mM Tris-HCl (pH 9.0 at 25° C.), 0.1% Triton X-100, 1.0 mM $MgCl_2$, 25 pmol of downstream primer ALD-2, 0.2 mM of each dNTP (Promega), 2.0 U of AMV reverse transcriptase (Promega) and 4.0 U of RNase inhibitor (Pharmacia). Minimal essential medium (MEM) was used as a negative control. Reverse transcription was carried out at 42° C. for 30 minutes, followed by inactivation of the reverse transcriptase at 95° C. for 5 minutes. Thirty µl of PCR-mix was then added to the reaction mixture. PCR-mix contains 50 mM KCl, 10 mM Tris-HCl (pH 9.0 at 25° C.), 0.1% Triton X-100, 1.0 mM $MgCl_2$, 25 pmol of the upstream primers ALD-1 and ALD-1b, 0.2 mM of each dATP, dCTP and dGTP, 0.19 mM of dTTP, 0.01 of digoxigenin-11-dUTP (Boehringer Manheim, Indianapolis, Ind.), and 1.25 U of Tth DNA polymerase (Promega). The reaction was carried out at 92° C. for 1 minute, 53° C. for 1 minute and 72° C. for 1 minute, for 10 cycles; 92° C. for 30 seconds, 55° C. for 30 seconds, and 72° C. for 30 seconds, for 30 cycles; followed by incubation at 72° C. for 5 minutes. Twelve µl of the sample was then subjected to electrophoresis in 2.2% agarose gels, and the gels were stained with ethidium bromide.

The remainder of the sample was extracted once with chloroform, precipitated in ethanol, and dissolved in 40 µl TE buffer (10 mM Tris-HCl, 1 mM EDTA, pH 7.4). As a negative control, hybridization buffer alone was used. For each hybridization reaction, 1 µl of the resuspended PCR product was diluted in 0.1 ml solution containing 50% formamide, 0.75M sodium chloride, 5 mM sodium phosphate (pH 7.0), 50 µg/ml sonicated and denatured salmon sperm DNA, 0.1% Tween-20, and 5 mM EDTA. For each serotype determination, these samples were added to four separate microwells, each coated one of the four dengue virus serotype-specific probes. Duplicate samples were run for each serotype-specific probe. The plates were sealed with adhesive tape and incubated in a 64° C. water bath.

After two hours, the plates were washed 6 times with 2xSSC, 0.1% SDS, followed by two stringent washes. For the stringent washes, 0.1xSSC, 0.1% SDS (0.2 ml) was added to each plate, and the plates were incubated at 68° C. for ten minutes. The plates were again washed 6 times with PBST, and 0.1 ml of peroxidase-conjugated sheep anti-digoxigenin Fab fragment (Boehringer Manheim), diluted 1:4000 in PBST, was added. The plates were incubated for one hour at room temperature on a plate shaker. After washing the plates 6 times with PBST, 0.2 ml substrate (0.04% o-phenylenediamine dihydrochloride, 0.012% hydrogen peroxide (Sigma Fast; Sigma)) was added to each well. After thirty minutes in the dark, the reaction was stopped by adding 50 µl 3N hydrochloric acid, and the absorbance at 490 nm of each well was determined using a microplate colorimetric reader.

This method was used to determine the serotypes of dengue reference viruses that had been serially diluted. As shown in FIG. 1, each of the probes recognized the serotype for which the probe was specific, but not the other dengue serotypes. This test can detect dengue virus at a concentration of 1.4 focus forming units (FFU) per reaction.

Figure 2:
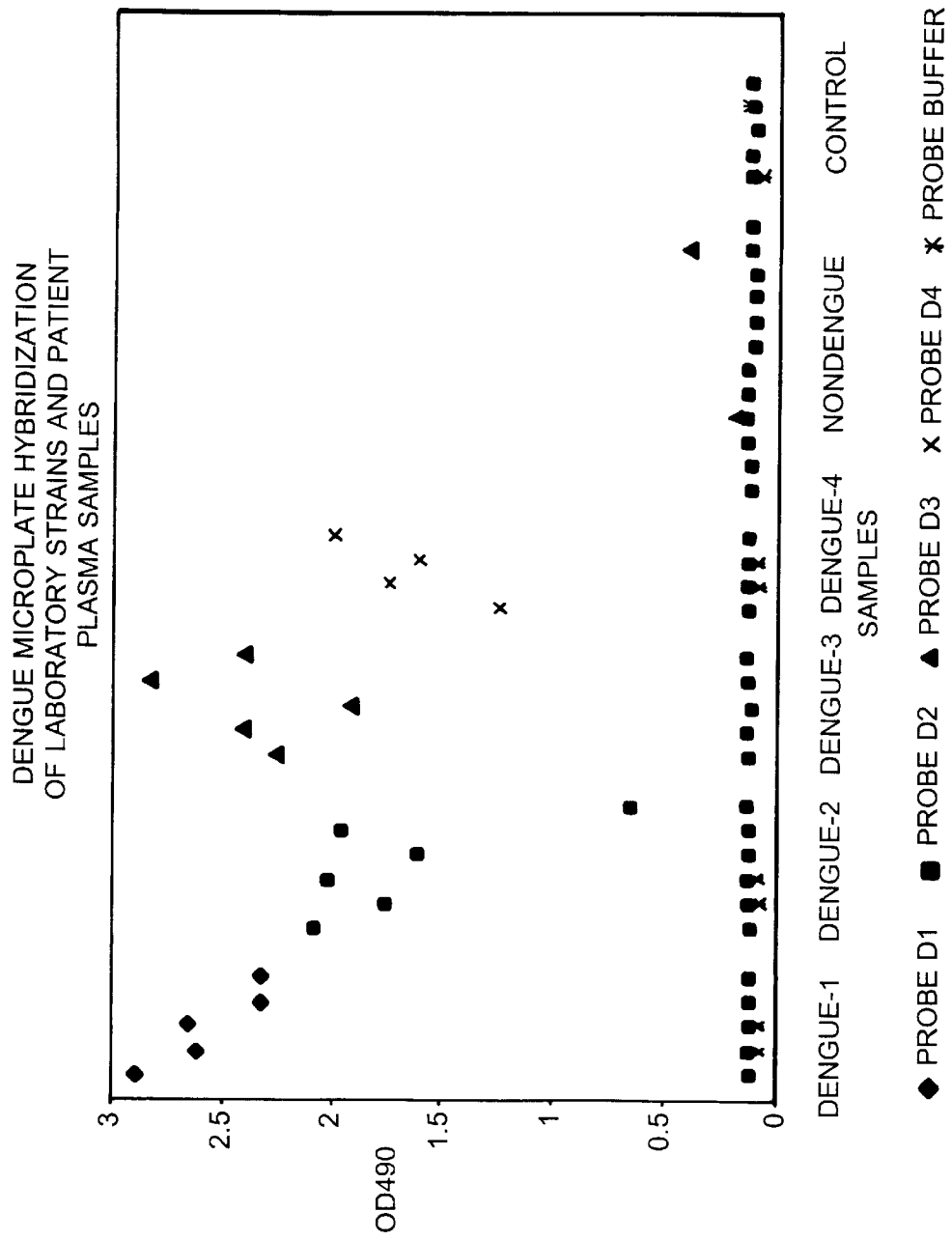
FIG. 2 is a graph showing the results of microplate reverse hybridization reactions of patient samples and reference strains of dengue virus to serotype-specific probes.

A set of laboratory strains of dengue viruses (den-1 Mochizuki strain, den-2 M11355 strain, den-2 Thai257 strain, den-3 Srilanka 904 strain, den-3 Srilanka 969 strain and den-4 H421 strain), was tested using this method, as well as plasma samples from patients known to be infected with a particular serotype of dengue virus (as determined by mosquito inoculation and enzyme immunoassay tests), and plasma samples from febrile patients who were not infected with dengue virus (as determined by mosquito inoculation assay and antibody or serological testing). The results of these experiments are shown in FIG. 2. Specific dengue virus serotypes were accurately detected. Thirteen plasma samples from febrile patients who were not infected with dengue virus were all negative by RT-PCR and ethidium bromide staining, but one showed a weak reaction with the dengue-3 probe in the microplate assay.

Other Embodiments

It is to be understood that while the invention has been described in conjunction with the detailed description thereof, the foregoing description is intended to illustrate and not limit the scope of the invention, which is defined by the scope of the appended claims. Other aspects, advantages and modifications are within the scope of the claims.

What is claimed is:

1. A method of detecting dengue virus and not Japanese encephalitis virus in a biological sample, said method comprising the steps of:

incubating RNA extracted from the sample with reverse transcriptase and a first dengue virus-specific primer including at least 15 consecutive nucleotides of SEQ ID NO:3, wherein the first dengue virus-specific primer is complementary to a portion of the 3' noncoding region in the dengue viral nucleic acid, for a time and under conditions sufficient to allow double stranded nucleic acid to form;

adding a second dengue virus-specific primer including at least 15 consecutive nucleotides of SEQ ID NO:1, wherein the second dengue virus-specific primer is identical to a portion of the 3' noncoding region in the dengue viral nucleic acid, and a thermostable DNA polymerase;

incubating for a time and under conditions sufficient to allow said double stranded nucleic acid, if any, to be amplified by polymerase chain reaction to form reaction products; and detecting the reaction products as an indication of the presence of dengue virus and not Japanese encephalitis virus in the sample.

2. The method of claim 1, wherein a third dengue virus-specific primer is added along with the second primer, wherein the third primer includes at least 15 consecutive nucleotides of SEQ ID NO:2, wherein the second dengue virus-specific primer is identical to a portion of the 3' noncoding region in the dengue viral nucleic acid.

3. A method of claim 2, wherein the third primer consists of the nucleotide sequence of SEQ ID NO:2.

4. A method of claim 1, wherein the first primer consists of the nucleotide sequence of SEQ ID NO:3.

5. A method of claim 1, wherein the second primer consists of the nucleotide sequence of SEQ ID NO:1.

6. A kit for detecting dengue virus and not Japanese encephalitis virus in a sample, the kit comprising:

a first dengue virus-specific primer including at least 15 consecutive nucleotides of SEQ ID NO:3, wherein the first dengue virus-specific primer is complementary to a portion of the 3' noncoding region in the dengue viral nucleic acid;

a second dengue virus-specific primer including at least 15 consecutive nucleotides of SEQ ID NO:1, wherein the second dengue virus-specific primer is identical to a portion of the 3' noncoding region in the dengue viral nucleic acid; and reagents for performing reverse-transcriptase-polymerase chain reaction (RT-PCR).

7. The kit of claim 6, further comprising a third dengue virus-specific primer including at least 15 consecutive nucleotides of SEQ ID NO:2, wherein the second dengue virus-specific primer is identical to a portion of the 3' noncoding region in the dengue viral nucleic acid.

8. A kit of claim 7, wherein the third primer consists of the nucleotide sequence of SEQ NO:2.

9. A kit of claim 6, wherein the first primer consists of the nucleotide sequence of SEQ ID NO:3.

10. A kit of claim 6, wherein the second primer consists of the nucleotide sequence of SEQ ID NO:1.

11. An isolated nucleic acid including at least 15 consecutive nucleotides of SEQ ID NO:3, wherein the nucleic acid is complementary to a portion of the 3' noncoding region in the dengue viral nucleic acid.

12. The nucleic acid of claim 11 consisting of the nucleotide sequence of SEQ ID NO:3.

13. An isolated nucleic acid including at least 15 consecutive nucleotides of SEQ ID NO:1, wherein the nucleic acid is identical to a portion of the 3' noncoding region in the dengue viral nucleic acid.

14. The nucleic acid of claim 13 consisting of the nucleotide sequence of SEQ ID NO:1.

15. An isolated nucleic acid including at least 15 consecutive nucleotides of SEQ ID NO:2, wherein the nucleic acid is identical to a portion of the 3' noncoding region in the dengue viral nucleic acid.

16. The nucleic acid of claim 15 consisting of the nucleotide sequence of SEQ ID NO:2.

17. An isolated nucleic acid including at least 15 consecutive nucleotides of SEQ ID NO:6, wherein the nucleic acid is identical to a portion of the 3' noncoding region in the dengue viral nucleic acid.

18. The nucleic acid of claim 17 consisting of the nucleotide sequence of SEQ ID NO:6.

* * * * *

SEQUENCE LISTING (1) GENERAL INFORMATION:

(iii) NUMBER OF SEQUENCES: 14

(2) INFORMATION FOR SEQ ID NO:1:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:1:

AAACCGTGCT GCCTGTAG

18

(2) INFORMATION FOR SEQ ID NO:2:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:2:

AAACTGTGCA GCCTGTAG

18

(2) INFORMATION FOR SEQ ID NO:3:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:3:

TCTCTCCCAG CGTCAATA

18

(2) INFORMATION FOR SEQ ID NO:4:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:4:

TCTCTCCCAG CGTCAA

16

(2) INFORMATION FOR SEQ ID NO:5:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:5:

TCTCCCAGCG TCAATA

16

(2) INFORMATION FOR SEQ ID NO:6:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:6:

AAACCGTGCA GCCTGTAG

18

(2) INFORMATION FOR SEQ ID NO:7:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:7:

TCTGGTCTCT CCCAGCGTCA ATATGCTG

28

(2) INFORMATION FOR SEQ ID NO:8:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:8:

TCTTTCCCAG CGTCAATA

18

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:9:

TGAGCAAACC GTGCTGCCTG TAGCTTCA

28

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:10:

TGAGCAAACC GTGCTGCCTG TAGCTCCG        28

(2) INFORMATION FOR SEQ ID NO:11:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:11:

TGAGTAAACT GTGCAGCCTG TAGCTCCA        28

(2) INFORMATION FOR SEQ ID NO:12:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:12:

TGAGCAAACT GTGCAGCCTG TAGCTCAC        28

(2) INFORMATION FOR SEQ ID NO:13:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: DNA (xi) SEQUENCE DESCRIPTION: SEQ ID NO:13:

TCTGGTCTCT CCCAGCGTCA ATATGCTG        28

(2) INFORMATION FOR SEQ ID NO:14:

```
    (i) SEQUENCE CHARACTERISTICS:
        (A) LENGTH: 28 base
pairs
        (B) TYPE: nucleic acid
        (C) STRANDEDNESS: single
        (D) TOPOLOGY: linear (ii) MOLECULE TYPE: DNA (xi) SEQUENCE DESCRIPT
ION: SEQ ID NO:14:

TCTGGTCTTT CCCAGCGTCA ATATGCTC
            28
```